United States Patent [19]

Goto et al.

[11] 4,413,005
[45] Nov. 1, 1983

[54] CARBAMATE DERIVATIVES AND INSECTICIDAL, MITICIDAL OR NEMATOCIDAL COMPOSITIONS CONTAINING THE SAME

[75] Inventors: Takeshi Goto, Naruto; Hisashi Takao, Tokushima; Takashi Soeda, Naruto; Nobuyoshi Asai; Sadahiko Iida, both of Tokushima; Mitsuyasu Kawata, Naruto; Norio Osaki, Naruto; Norio Yasudomi, Naruto; Tadateru Murata, Tokushima; Akira Tanaka, Naruto, all of Japan

[73] Assignee: Otsuka Kagaku Yakuhin Kabushiki Kaisha, Osaka, Japan

[21] Appl. No.: 352,862

[22] Filed: Feb. 26, 1982

[30] Foreign Application Priority Data

Jun. 2, 1981 [JP] Japan .................................. 56-85093
Jun. 2, 1981 [JP] Japan .................................. 56-85094
Aug. 7, 1981 [JP] Japan .................................. 56-124422
Aug. 7, 1981 [JP] Japan .................................. 56-124423

[51] Int. Cl.$^3$ .................... A01N 47/24; C07D 307/86
[52] U.S. Cl. ..................................... 424/285; 549/470
[58] Field of Search ........................ 549/470; 424/285

[56] References Cited

U.S. PATENT DOCUMENTS 3,843,688 10/1974 Cleveland ...................... 260/346.73

Primary Examiner—John M. Ford
Assistant Examiner—Bernard Dentz
Attorney, Agent, or Firm—Armstrong, Nikaido, Marmelstein & Kubovcik

[57] ABSTRACT

This invention relates to carbamate derivatives represented by the formula (I):

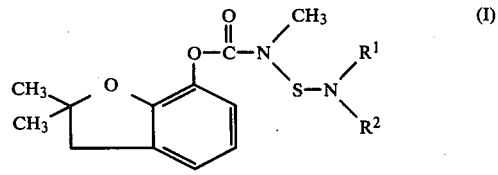

a process for preparing the derivatives and insecticides containing the derivatives.

12 Claims, No Drawings

CARBAMATE DERIVATIVES AND INSECTICIDAL, MITICIDAL OR NEMATOCIDAL COMPOSITIONS CONTAINING THE SAME

This invention relates to carbamate derivatives, insecticidal, miticidal or nematocidal compositions containing the derivatives as an active ingredient, a process for preparing such derivatives, and a method for controlling noxious insects, mites or nematodes. In the present specification, the term "insecticidal" includes "miticidal" and "nematocidal" in addition to "insecticidal", and the term "insect(s)" includes "mite(s)" and "nematode(s)" in addition to "insect(s)", respectively, unless otherwise indicated.

It is known that some carbamate compounds have high insecticidal activity, and they include those actually in use. However, many of such carbamate compounds have the drawback of being toxic or warm-blooded animals. Above all, 2,3-dihydro-2,2-dimethyl-benzofuran-7-yl N-methyl-carbamate (hereinafter referred to as "carbofuran", as generally called) is known to have high insecticidal activity, but it causes problems in practical use due to high toxicity to warm-blooded animals. Accordingly, if it is possible to prepare carbamate compounds which are comparable to carbofuran in insecticidal activity and yet have reduced toxicity to warm-blooded animals, the compounds should be very useful. From this viewpoint, various carbofuran sulfenyl compounds have been synthesized, and the relation between their insecticidal activity and toxicity to warm-blooded animals is being investigated, with reports made on the results of investigations. For example, Belgian Patent 817,517 discloses 2,3-dihydro-2,2-dimethylbenzofuran-7-yl N-(N,N-dibutylaminosulfenyl)-N-methyl-carbamate, and German Patent DT-OS 2,254,359 discloses 2,3-dihydro-2,2-dimethylbenzofuran-7-yl N-(N-methyl-N-benzenesulfonylaminosulfenyl)-N-methyl-carbamate. These compounds nevertheless fail to fully fulfill the requirements in respect of insecticidal activity, toxicity to warm-blooded animal and to fish and manufacturing process.

We have conducted intensive research in an attempt to develop carbamate compounds which will fulfill all of such requirements and found that the contemplated objects can be achieved by compounds represented by the formula (I):

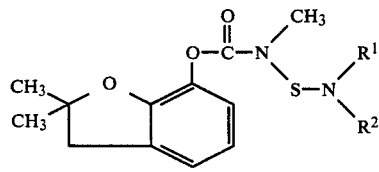

wherein $R^1$ and $R^2$, which may be the same or different, each represents (1) —X—COOR$^3$, in which X represents an alkylene group having 1 to 6 carbon atoms, and $R^3$ represents an alkyl group having 1 to 8 carbon atoms or a cycloalkyl group having 3 to 6 carbon atoms; or (2) —Y—CN, in which Y represents an alkylene group having 1 to 6 carbon atoms; and $R^2$ further represents an alkyl group having 1 to 8 carbon atoms; a cycloalkyl group having 3 to 6 carbon atoms; a benzyl group which may be substituted with a halogen atom, an alkyl group having 1 to 3 carbon atoms or an alkoxy group having 1 to 3 carbon atoms; a phenyl group which may be substituted with a halogen atom, an alkyl group having 1 to 3 carbon atoms or an alkoxy group having 1 to 3 carbon atoms; or —Z—R$^4$, in which Z represents a carbonyl group or a sulfonyl group, and R$^4$ represents an alkyl group having 1 to 6 carbon atoms which may be substituted with a halogen atom, a phenyl group which may be substituted with a halogen atom, an alkyl group having 1 to 3 carbon atoms or an alkoxy group having 1 to 3 carbon atoms, a benzyl group, an alkoxy group having 1 to 6 carbon atoms or a phenoxy group.

In the definition for the formula (I) above, the alkyl moiety in the alkyl group, alkylene group and alkoxy group may be straight chain or branched chain.

Compounds represented by the formula (I'):

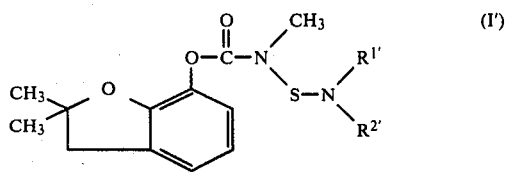

wherein $R^{1'}$ and $R^{2'}$, which may be the same or different, each represents (1) —X'—COOR$^{3'}$, in which X' represents an alkylene group having 1 to 2 carbon atoms, and $R^{3'}$ represents an alkyl group having 1 to 4 carbon atoms which may be straight chain or branched chain; or (2) —Y'—CN, in which Y' represents an alkylene group having 1 to 2 carbon atoms; and $R^{2'}$ further represents an alkyl group having 1 to 6 carbon atoms which may be straight chain or branched chain, or a cycloalkyl group having 3 to 6 carbon atoms, are preferred in this invention.

Thus, this invention has been accomplished.

The compounds of the formula (I) are novel compounds which have not been disclosed in any literature and which have been discovered by us for the first time. We have found that the novel compounds have outstanding insecticidal activity or controlling effect on agricultural and forestry noxious insects and household noxious insects and are comparable in such effect to carbofuran which has the highest insecticidal activity heretofore known. The compounds are effective on a wide variety of noxious insects, mites and nematodes which are harmful to vegetables, trees, other plants and man, such as Hemiptera, Lepidoptera, Coleoptera, Diptera, Thysanoptera, Orthoptera, Isopoda, Acarina, Tylenchida, etc. Examples of these insects, mites and nematodes are as follows.

Hemiptera
 (1) Deltocephalidae: *Nephotettix cincticeps*
 (2) Delphacidae: *Laodelphax striatellus, Nilaparvata lugens*
 (3) Aphididae: *Myzus persicae, Aphis gossypii*
 (4) Pentatomidae: *Nezara antennata, Nezara viridula*
Lepidoptera
 (1) Noctuidae: *Spodoptera litura, Agrotis fucosa, Laphygma exigua*
 (2) Tortricidae: *Adoxophyes orana*
 (3) Pyralidae: *Chilo suppressalis, Ostrinia furnacalis, Cnaphalocrocis medinalis*
 (4) Plutellidae: *Plutella xylostella*
Coleoptera
 (1) Curculionidae: *Echinocnemus squameus, Lissorhoptrus oryzophilus*
 (2) Scarabaeidae: *Popillia japonica*
 (3) Coccinellidae: *Henosepilachna vigintioctopunctata*
Diptera (1) Muscidae: *Musca domestica*
(2) Cecidomyiidae: Aspondylia sp.
(3) Agromyzidae: *Phytobia cepae*

Thysanoptera
  Thripidae: *Thrips tabaci, Scirtothrips dorsalis*

Orthoptera
  Gryllotalpidae: *Gryllotalpa africana*

Isopoda
  Armandillidae: *Armadillidium vulgare*

Acarina
  Tetranychidae: *Tetranychus telarius, Tetranychus urticae, Panonychus citri*

Tylenchida
  Heteroderidae: *Meloidogyne incognita*

The toxicity of the carbamate derivatives of the formula (I) to warm-blooded animals is as low as about 1/5 to about 1/100 the toxicity of carbofuran. The present compounds exhibit insecticidal activity or controlling effect on the above-mentioned organisms in any stage or a specific stage of their growth and are therefore effectively usable for controlling them in the fields of agriculture, forestry and sanitation.

The present compounds of the formula (I) are very easy to prepare with high purities in high yields and have great commercial advantages as will be described in detail later.

Typical of the compounds of the formula (I) are those as described in Examples 1 to 56 set forth hereinafter. Of these compounds, the following compounds are particularly preferred in this invention.

2,3-Dihydro-2,2-dimethylbenzofuran-7-yl N-[N,N-bis-(ethoxycarbonylmethyl)aminosulfenyl]-N-methylcarbamate 2,3-Dihydro-2,2-dimethylbenzofuran-7-yl N-(N-methyl-N-ethoxycarbonylmethylaminosulfenyl)-N-methylcarbamate 2,3-Dihydro-2,2-dimethylbenzofuran-7-yl N-(N-isopropyl-N-ethoxycarbonylethylaminosulfenyl)-N-methylcarbamate 2,3-Dihydro-2,2-dimethylbenzofuran-7-yl N-(N-n-butyl-N-ethoxycarbonylethylaminosulfenyl)-N-methylcarbamate 2,3-Dihydro-2,2-dimethylbenzofuran-7-yl N-(N-cyclohexyl-N-ethoxycarbonylethylaminosulfenyl)-N-methylcarbamate 2,3-Dihydro-2,2-dimethylbenzofuran-7-yl N-(N-n-butyl-N-cyanoethylaminosulfenyl)-N-methyl-carbamate The compounds of the formula (I) can be prepared, for example, by reacting a compound represented by the formula (II):

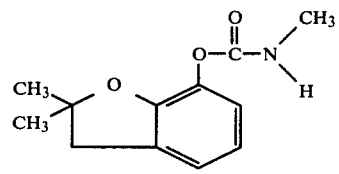
(II)

with sulfur dichloride to form 2,3-dihydro-2,2-dimethylbenzofuran-7-yl N-(chlorosulfenyl)-N-methyl-carbamate represented by the formula (III):

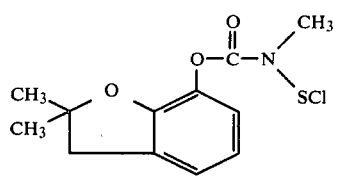
(III)

which is then reacted with an amine compound represented by the formula (IV):

(IV)

wherein $R^1$ and $R^2$ are as defined above.

The reaction of the compound of the formula (II) with sulfur dichloride may be conducted in the presence or absence of a solvent. Examples of useful solvents are methylene chloride, chloroform, carbon tetrachloride and like hydrocarbon halides, and diethyl ether, dibutyl ether, tetrahydrofuran, dioxane and like ethers, etc. The proportions of the compound of the formula (II) and $SCl_2$ are not particularly limited but are widely variable suitably. Usually 1 to 2 moles, preferably about 1 to about 1.2 moles, of the latter is used per mole of the former. Preferably the reaction is conducted in the presence of a basic compound. Examples of useful basic compounds are triethylamine, tributylamine, dimethylaniline, diethylaniline, ethylmorpholine and like tertiary amines, pyridine, $\alpha,\beta,\gamma$-picoline, lutidine, etc. The basic compound may be used in an amount sufficient to capture the hydrogen chloride to be produced by the reaction as a by-product. Usually 1 to 2 moles of the basic compound is used per mole of the compound of the formula (II). The reaction, which proceeds with cooling, at room temperature or with heating, is carried out usually at $-70°$ to $50°$ C., preferably about $-10°$ to about $30°$ C. The reaction time is about 2 to about 7 hours, preferably about 3 to about 5 hours. The compound (III) is subsequently reacted with an amine compound of the formula (IV).

Examples of useful amine compounds of the formula (IV) are those secondary amines represented by the formulae (V) to (IX):

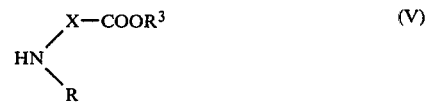
(V)

(VI)

(VII)

(VIII)

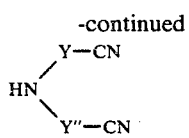
(IX)

In the formulae (V) to (IX), X, Y, and $R^3$ are as defined above; R represents an alkyl group having 1 to 8 carbon atoms; a cycloalkyl group having 3 to 6 carbon atoms; a benzyl group which may be substituted with a halogen atom, an alkyl group having 1 to 3 carbon atoms or an alkoxy group having 1 to 3 carbon atoms; a phenyl group which may be substituted with a halogen atom, an alkyl group having 1 to 3 carbon atoms or an alkoxy group having 1 to 3 carbon atoms, or $Z'-R^{4'}$, in which $Z'$ represents a carbonyl group or a sulfonyl group, and $R^{4'}$ represents an alkyl group having 1 to 6 carbon atoms which may be substituted with a halogen atom, a phenyl group which may be substituted with a halogen atom, an alkyl group having 1 to 3 carbon atoms or an alkoxy group having 1 to 3 carbon atoms, a benzyl group, an alkoxy group having 1 to 6 carbon atoms or a phenoxy group (in which the alkyl group and alkoxy group may be straight or branched chain); $R^{3''}$ has the same meaning as in $R^3$; $X''$ has the same meaning as in X; and $Y''$ has the same meaning as in Y.

Representative examples of the amine compound of the formula (V) are N-methylglycine methyl ester, N-methylglycine ethyl ester, N-methylglycine butyl ester, N-ethylglycine ethyl ester, N-n-propylglycine ethyl ester, N-isopropylglycine ethyl ester, N-n-butylglycine ethyl ester, N-isobutylglycine ethyl ester, N-sec-butylglycine ethyl ester, N-n-octylglycine ethyl ester, N-cyclohexylglycine ethyl ester, N-benzylglycine ethyl ester, N-(4-methylbenzyl)glycine ethyl ester, N-(4-chlorobenzyl)glycine ethyl ester, N-phenylglycine ethyl ester, N-(3-methylphenyl)glycine ethyl ester, N-(4-methoxyphenyl)glycine ethyl ester, ethyl N-methylaminopropionate, ethy N-n-propylaminopropionate, methyl N-isopropylaminopropionate, ethyl N-isopropylaminopropionate, butyl N-isopropylaminopropionate, 2-ethylhexyl N-isopropylaminopropionate, methyl N-n-butylaminopropionate, ethyl N-n-butylaminopropionate, ethyl N-isobutylaminopropionate, ethyl N-sec-butylaminopropionate, ethyl N-t-butylaminopropionate, ethyl N-n-amylaminopropionate, ethyl N-isoamylaminopropionate, ethyl N-n-hexylaminopropionate, ethyl N-cyclohexylaminopropionate, N-acetylglycine ethyl ester, N-chloroacetylaminoglycine ethyl ester, N-propionylglycine ethyl ester, N-benzoylglycine ethyl ester, N-(4-chlorobenzoyl)glycine ethyl ester, N-tosylglycine ethyl ester, etc.

Representative examples of the amine compound of the formula (VI) are N-methylaminoacetonitrile, N-ethylaminoacetonitrile, N-n-propylaminoacetonitrile, N-isopropylaminoacetonitrile, N-n-butylaminoacetonitrile, N-isobutylaminoacetonitrile, N-benzylaminoacetonitrile, N-phenylaminoacetonitrile, N-(4-methylphenyl)aminoacetonitrile, N-methylaminopropionitrile, N-n-propylaminopropionitrile, N-isopropylaminopropionitrile, N-n-butylaminopropionitrile, N-isobutylaminopropionitrile, N-sec-butylaminopropionitrile, N-octylaminopropionitrile, N-cyclohexylaminopropionitrile, etc.

Representative examples of the amine compound of the formula (VII) are methyl iminodiacetate, ethyl iminodiacetate, isopropyl iminodiacetate, cyclohexyl iminodiacetate, methyl iminodipropionate, ethyl iminodipropionate, N-methoxycarbonylglycine ethyl ester, N-ethoxycarbonylglycine ethyl ester, N-phenoxycarbonylglycine ethyl ester, ethyl N-ethoxycarbonylmethylaminopropionate, ethyl 4-(ethoxycarbonylmethylamino)butyrate, ethyl 2-(ethoxycarbonylmethylamino)butyrate, ethyl N-ethoxycarbonylaminopropionate, etc.

Representative examples of the amine compound of the formula (VIII) are methyl N-cyanomethylcarbamate, ethyl N-cyanomethylcarbamate, ethyl N-cyanoethylcarbamate, N-cyanomethylglycine ethyl ester, N-cyanoethylglycine ethyl ester, ethyl N-cyanomethylaminopropionate, ethyl N-cyanoethylaminopropionate, etc.

Representative examples of the amine compound of the formula (IX) are iminodiacetonitrile, iminodipropionitrile, iminodibutyronitrile, etc.

The reaction of the compound of the formula (III) with the amine compound of the formula (IV) may be conducted in the presence or absence of a solvent. Any of the solvents useful for reacting the compound of the formula (II) with sulfur dichloride is usable for this reaction. The proportions of the compound of the formula (III) and the amine are not particularly limited but are widely variable suitably. Usually about 1 to about 2 moles, preferably about 1 to about 1.2 moles, of the latter is used per mole of the former. It is preferable to conduct this reaction also in the presence of a basic compound, which can be any one of those already mentioned. The basic compound may be used in such an amount that is sufficient to capture the hydrogen chloride to be formed by the reaction as a by-product. Usually 1 to 2 moles, preferably 1 to 1.5 moles, of the basic compound is used per mole of the compound (III). The reaction, which proceeds with cooling, at room temperature or with heating, is carried out usually at $-20°$ to $50°$ C., preferably $0°$ to $30°$ C. The reaction time is usually about 10 to about 15 hours.

The compound of this invention represented by the formula (I) and thus obtained can be easily isolated and purified by a usual method of separation, such as solvent extraction, recrystallization or chromatography.

The compounds (I) of this invention can be formulated into emulsions, wettable powders, suspensions, concentrated suspensions, granules, fine particles, pellets, dusts, coating compositions, foam sprays, aerosols, microcapsule compositions, impregnants to be applied to natural or synthetic materials, fumigants, concentrated preparations to be applied in small amounts, etc.

Various surfactants are usable for the preparations of such emulsions, dispersions, suspensions and foams. Examples of useful nonionic surfactants are polyoxyethylene alkyl ethers, polyoxyethylene alkyl esters, polyoxyethylene sorbitan alkyl esters, sorbitan alkyl esters, etc. Examples of useful anionic surfactants are alkylbenzenesulfonates, alkyl sulfosuccinates, alkyl sulfates, polyoxyethylene alkylether sulfates, alkylnaphthalene sulfonates, lignin sulfonates, etc.

Solvents, diluting agents and carriers for the present compounds include various organic solvents, aerosol propellants, natural minerals, vegetables, synthetic compounds, etc. Examples of preferred organic solvents are benzene, toluene, xylene, ethylbenzene, chlorobenzene, alkylnaphthalenes, dichloromethane, chloroethylene, cyclohexane, cyclohexanone, acetone, methyl ethyl ketone, methyl isobutyl ketone, alcohols, dimethylformamide, dimethyl sulfoxide, acetonitrile, fractions of mineral oils, etc. Examples of useful aerosol propellants are propane, butane, hydrocarbon carbon halides, nitrogen, carbon dioxide, etc. Examples of useful natural minerals are kaolin, talc, bentonite, diatomaceous earth, clay, montmorillonite, chalk, calcite, pumice, dolomite, etc. Examples of useful vegetables are coconut shells, tobacco stalks, sawdust, etc. Exemplary of useful synthetic compounds are alumina, silicates, sugar polymers, etc. Also useful are adhesives, such as carboxymethyl cellulose, gum arabic, polyvinyl alcohol, polyvinyl acetate, etc. The preparations can be colored with organic or inorganic dyes.

The compounds (I) of this invention are formulated into various preparations, such as those exemplified above, so that the preparations contain, as an active ingredient, an insecticidally, miticidally or nematocidally effective amount (e.g., about 0.1 to about 95% by weight, preferably about 0.5 to about 90% by weight) of the compound. Depending on the application contemplated, such preparations are used as such, or as diluted with a carrier or water.

The present invention will be described below in greater detail with reference to the following examples.

EXAMPLE 1

Preparation of
2,3-dihydro-2,2-dimethylbenzofuran-7-yl
N-[N,N-bis(cyanomethyl)aminosulfenyl]-N-methylcarbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at 0° C. The mixture was stirred at the same temperature for 2 hours, a solution of 4.8 g (0.05 mole) of iminodiacetonitrile in 40 ml of tetrahydrofuran was then added dropwise to the mixture at the same temperature, and 5 g (0.05 mole) of triethylamine was further added dropwise to the mixture. The resulting mixture was stirred at 0° C. for 4 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product, which was almost entirely composed of the desired product although containing small amounts of the starting materials. Yield: 13.8 g (79.8%).

For the identification of the product, a portion thereof was purified by silica gel column chromatography, using benzene/ethyl acetate (4:1) as the solvent, whereby a crystal having a melting point of 94° to 95° C. was obtained.

| NMR in chloroform-d₁: | |
|---|---|
| δ 1.48 ppm (s, 6H) | δ 3.02 ppm (s, 2H) |
| δ 3.50 ppm (s, 3H) | δ 4.32 ppm (s, 4H) |
| δ 6.6–7.2 ppm (m, 3H) | |
| Elemental Analysis: | |

| | C | H | N |
|---|---|---|---|
| Found (%): | 55.36 | 5.31 | 16.05 |
| Calcd. for C₁₆H₁₈N₄O₃S: (molecular wt. 346.418) | 55.48 | 5.24 | 16.17 |

Thus, the product was confirmed to have the following formula:

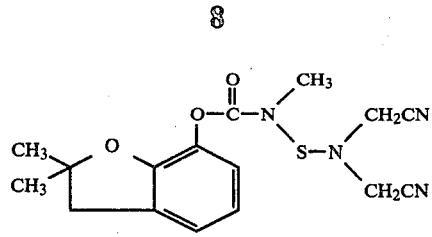

EXAMPLE 2

Preparation of
2,3-dihydro-2,2-dimethylbenzofuran-7-yl
N-[N,N-bis(ethoxycarbonylmethyl)aminosulfenyl]-N-methylcarbamate A 11 g quantity (0.05 mole) of 2,3-dihydro-2,2-dimethylbenzofuran-7-yl N-methyl-carbamate was dissolved in 50 ml of chloroform, 5.2 g (0.05 mole) of sulfur dichloride was added to the solution with cooling, and 5 g (0.05 mole) of triethylamine was further added dropwise to the solution at 0° C. The mixture was stirred at the same temperature for 2 hours, a solution of 9.5 g (0.05 mole) of ethyl iminodiacetate in 20 ml of chloroform was then added dropwise to the mixture at the same temperature, and 5 g (0.05 mole) of triethylamine was further added dropwise to the mixture. The resulting mixture was stirred at 0° C. for 2 hours and thereafter allowed to stand overnight at room temperature. With addition of 100 ml of chloroform, the reaction mixture was washed with 100 ml of water three times. The chloroform layer was dried and then concentrated in a vacuum to give an oily product, which was almost entirely composed of the desired product although containing small amounts of the starting materials. Yield: 15.9 g (72.3%).

For the identification of the product, a portion thereof was purified by silica gel column chromatography, using benzene/ethyl acetate (4:1) as the solvent, whereby an oily product was obtained:

| NMR in chloroform-d₁: | |
|---|---|
| δ 1.24 ppm (t, 6H) | δ 1.48 ppm (s, 6H) |
| δ 3.02 ppm (s, 2H) | δ 3.42 ppm (s, 3H) |
| δ4.20 ppm (q, 4H) | δ 4.28 ppm (s, 4H) |
| δ 6.6–7.2 ppm (m, 3H) | |
| Elemental Analysis: | |

| | C | H | N |
|---|---|---|---|
| Found (%): | 54.68 | 6.46 | 6.38 |
| Calcd. for C₂₀H₂₈N₂O₇S: (molecular wt. 440.526) | 54.53 | 6.41 | 6.36 |

Thus, the product was confirmed to have the following formula:

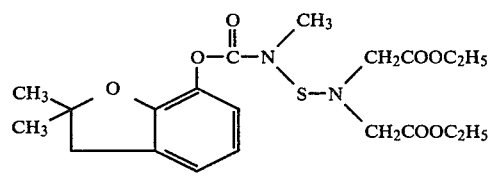

EXAMPLES 3 TO 5

The compounds shown in Table 1 below were prepared in the same manner as in Example 1 or 2. The physical properties and NMR data (in chloroform-d₁) of these compounds are also shown in Table 1.

TABLE 1

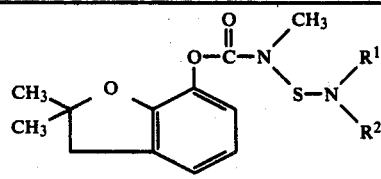

| Example No. | Amine | R¹ | R² | H-NMR [δ Value (ppm) in CDCl₃] | Elemental Analysis Empirical Formula Found Value (Calculated Value) | | |
|---|---|---|---|---|---|---|---|
| | | | | | C (%) | H (%) | N (%) |
| 3 | HN(CH₂COOCH₃)₂ | —CH₂COOCH₃ | —CH₂COOCH₃ | δ1.47 (s, 6H), δ3.02 (s, 2H), δ3.41 (s, 3H), δ3.73 (s, 6H), δ4.30 (s, 4H), δ6.7–7.2 (m, 3H) | $C_{18}H_{24}N_2O_7S$ 52.11 (52.42) | 5.91 (5.87) | 6.63 (6.79) |
| 4 | HN(CH₂COO-iPr)₂ | —CH₂COO-iPr | —CH₂COO-iPr | δ1.23 (d, 6H), δ1.46 (s, 6H), δ3.03 (s, 2H), δ3.42 (s, 3H), δ4.26 (s, 4H), δ4.5–5.3 (m, 1H), δ6.6–7.2 (m, 3H) | $C_{22}H_{32}N_2O_7S$ 56.3 (56.40) | 6.91 (6.89) | 5.86 (5.98) |
| 5 | HN(CH₂COO-C₆H₁₁)₂ | —CH₂COO-C₆H₁₁ | —CH₂COO-C₆H₁₁ | δ1.0–2.2 (m, 20H), δ1.48 (s, 6H), δ3.02 (s, 2H), δ3.43 (s, 3H), δ4.28 (s, 4H), δ4.5–5.1 (m, 2H), δ6.7–7.2 (m, 3H) | $C_{28}H_{40}N_2O_7S$ 61.32 (61.29) | 7.39 (7.35) | 4.95 (5.11) |

EXAMPLE 6

Preparation of 2,3-dihydro-2,2-dimethylbenzofuran-7-yl N-[N,N-bis(ethoxycarbonylethyl)aminosulfenyl]-N-methylcarbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at −10° to −5° C. The mixture was stirred at 0° C. for one hour and further at room temperature for 2 hours. After cooling to −10° to −5° C., 10.9 g (0.05 mole) of diethyl iminodipropionate was added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product, which was almost entirely composed of the desired product although containing small amounts of impurities. Yield: 16.9 g (72.2%).

For the identification of the product, a portion thereof was purified by silica gel column chromatography, using benzene/ethyl acetate (5:1) as the solvent, whereby an oily product was obtained.

NMR in chloroform-d₁:
δ 1.21 ppm (t, 6H)
δ 1.44 ppm (s, 6H)
δ 2.67 ppm (t, 4H)
δ 3.37 ppm (s, 3H)
δ 4.04 ppm (q, 4H)
δ 2.97 ppm (s, 2H)
δ 3.42 ppm (t, 4H)
δ 6.5–7.2 ppm (m, 3H)

Elemental Analysis:

| | C | H | N |
|---|---|---|---|
| Found (%): | 56.26 | 6.91 | 5.52 |
| Calcd. for $C_{22}H_{32}N_2O_7S$: (molecular wt. 468.58) | 56.39 | 6.88 | 5.98 |

Thus, the product was confirmed to have the following formula:

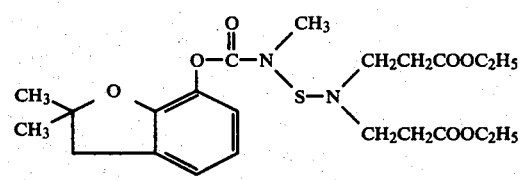

EXAMPLE 7

Preparation of 2,3-dihydro-2,2-dimethylbenzofuran-7-yl N-[N,N-bis(cyanoethyl)aminosulfenyl]-N-methyl-carbamate A 11 g quantity (0.05 mole) of 2,3-dihydro-2,2-dimethylbenzofuran-7-yl N-methyl-carbamate was dissolved in 50 ml of chloroform, 5.2 g (0.05 mole) of sulfur dichloride was added to the solution with cooling, and 5 g (0.05 mole) of triethylamine was further added dropwise to the solution at =10° to =5° C. The mixture was stirred at 0° C. for one hour and further at room temperature for one hour. After cooling to −10° to −5° C., 6.2 g (0.05 mole) of iminodipropionitrile was added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of chloroform, the reaction mixture was washed with 100 ml of water three times. The chloroform layer was dried and then concentrated in a vacuum to give an oily product, which was almost entirely composed of the desired product although containing small amounts of impurities. Yield: 12.2 g (65.2%).

For the identification of the product, a portion thereof was purified by silica gel column chromatography, using benzene/ethyl acetate (4:1) as the solvent, whereby an oily product was obtained.

| NMR in chloroform-$d_1$: | |
|---|---|
| δ 1.43 ppm (s, 6H) | δ 2.73 ppm (t, 4H) |
| δ 2.97 ppm (s, 2H) | δ 3.37 ppm (s, 3H) |
| δ 3.43 ppm (t, 4H) | δ 6.5–7.2 ppm (m, 3H) |

| Elemental Analysis: | | | |
|---|---|---|---|
| | C | H | N |
| Found (%): | 57.91 | 5.79 | 15.04 |
| Calcd. for $C_{18}H_{22}N_4O_3S$: (molecular wt. 374.47) | 57.73 | 5.92 | 14.96 |

Thus, the product was confirmed to have the following formula:

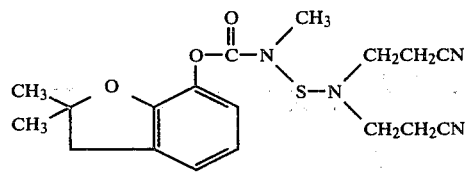

EXAMPLES 8 TO 11

The compounds shown in Table 2 below were prepared in the same manner as in Example 6 or 7. The physical properties and NMR data (in chloroform-$d_1$) of these compounds are also shown in Table 2.

TABLE 2

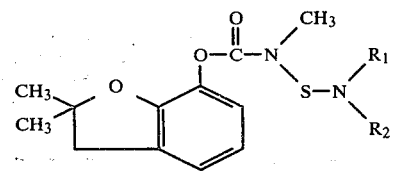

| Example No. | Amine | $R^1$ | $R^2$ | H-NMR [δ Value (ppm) in CDCl$_3$] | Elemental Analysis Empirical Formula Found Value (Calculated Value) | | |
|---|---|---|---|---|---|---|---|
| | | | | | C (%) | H (%) | N (%) |
| 8 | HN(CH$_2$CH$_2$CN)(CH$_2$COOC$_2$H$_5$) | —CH$_2$CH$_2$CN | —CH$_2$COOC$_2$H$_5$ | δ1.26 (t, 3H), δ1.47 (s, 6H), δ2.6–3.1 (m, 2H), δ3.02 (s, 2H), δ3.40 (s, 3H), δ3.3–3.8 (m, 2H), δ4.18 (s, 2H), δ4.20 (q, 2H), δ6.6–7.2 (m, 3H) | $C_{19}H_{25}N_3O_5S$ 55.89 (56.01) | 6.31 (6.19) | 10.64 (10.31) |
| 9 | HN(CH$_2$CH$_2$COOC$_2$H$_5$)(CH$_2$COOC$_2$H$_5$) | —CH$_2$CH$_2$COOC$_2$H$_5$ | —CH$_2$COOC$_2$H$_5$ | δ1.23 (t, 6H), δ1.45 (s, 6H), δ2.70 (t, 2H), δ3.00 (s, 2H), δ3.39 (s, 3H), δ3.40 (t, 2H), δ4.09 (q, 2H), δ4.14 (s, 2H), δ4.55 (q, 2H), δ6.5–7.2 (m, 3H) | $C_{21}H_{30}N_2O_7S$ 55.94 (55.50) | 6.79 (6.65) | 6.05 (6.16) |
| 10 | HN(CH$_2$CH$_2$CH$_2$COOC$_2$H$_5$)(CH$_2$COOC$_2$H$_5$) | —CH$_2$CH$_2$CH$_2$COOC$_2$H$_5$ | —CH$_2$COOC$_2$H$_5$ | δ1.22 (t, 6H), δ1.45 (s, 6H), δ1.7–2.6 (m, 4H), δ3.00 (s, 2H), δ3.35 (t, 2H), δ3.42 (s, 3H), δ4.13 (q, 2H), δ4.15 (s, 2H), δ4.17 (q, 2H), δ6.5–7.2 (m, 3H) | $C_{22}H_{32}N_2O_7S$ 55.94 (56.40) | 6.93 (6.89) | 6.25 (5.98) |

TABLE 2-continued

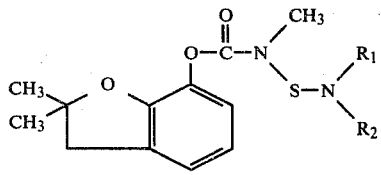

| Example No. | Amine | R¹ | R² | H-NMR [δ Value (ppm) in CDCl₃] | Elemental Analysis Empirical Formula Found Value (Calculated Value) | | |
|---|---|---|---|---|---|---|---|
| | | | | | C (%) | H (%) | N (%) |
| 11 | HN(CH₂CH₃)(CHCOOC₂H₅)(CH₂COOC₂H₅) | $-\underset{\underset{CHCOOC_2H_5}{|}}{CH_2CH_3}$ | $-CH_2COOC_2H_5$ | δ0.99 (t, 3H), δ1.20 (t, 3H), δ1.23 (t, 3H), δ1.43 (s, 6H), δ1.5–2.5 (m, 2H), δ3.02 (s, 2H), δ3.38 (s, 3H), δ3.5–4.5 (m, 7H), δ6.5–7.2 (m, 3H) | $C_{22}H_{32}N_2O_7S$ 56.53 (56.40) | 6.78 (6.89) | 5.81 (5.98) |

EXAMPLE 12

Preparation of 2,3-dihydro-2,2-dimethylbenzofuran-7-yl N-(N-butyl-N-ethoxycarbonylmethylaminosulfenyl)-N-methyl-carbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at −10° to −5° C. The mixture was stirred at 0° C. for one hour and further at room temperature for 2 hours. After cooling to −10° to −5° C., 8.0 g (0.05 mole) of N-butylglycine ethyl ester was added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product, which was almost entirely composed of the desired product although containing small amounts of impurities. Yield: 15.7 g (76.6%).

For the identification of the product, a portion thereof was purified by silica gel column chromatography, using hexane/ethyl acetate (4:1) as the solvent, whereby an oily product was obtained.

| NMR in chloroform-d₁: | |
|---|---|
| δ 0.6–1.9 ppm (m, 7H) | δ 1.22 ppm (t, 3H) |
| δ 1.44 ppm (s, 6H) | δ 3.03 ppm (s, 2H) |
| δ 3.30 ppm (t, 2H) | δ 3.42 ppm (s, 3H) |
| δ 4.14 ppm (s, 2H) | δ 4.13 ppm (q, 2H) |
| δ 6.5–7.2 ppm (m, 3H) | |

| Elemental Analysis: | | | |
|---|---|---|---|
| | C | H | N |
| Found (%): | 58.39 | 7.41 | 6.75 |
| Calcd. for C₂₀H₃₀N₂O₅S: (molecular wt. 410.54) | 58.52 | 7.37 | 6.83 |

Thus, the product was confirmed to have the following formula:

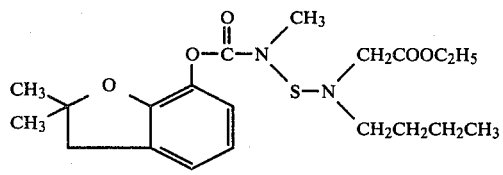

EXAMPLE 33

Preparation of 2,3-dihydro-2,2-dimethylbenzofuran-7-yl N-(N-phenyl-N-ethoxycarbonylmethylaminosulfenyl)-N-methylcarbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at −10° to −5° C. The mixture was stirred at 0° C. for one hour and further at room temperature for 2 hours. After cooling to −10° to −5° C., 9 g (0.05 mole) of N-phenylglycine ethyl ester was then added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product. A benzene-hexane (1:1) mixture was added to the oily product, whereby crystals were precipitated. The thus-precipitated crystals were then filtered off, and the mother liquor was concentrated to give an oily product, which was subsequently cooled to obtain crystals. The thus-obtained crystals were recrystallized from diethyl ether to obtain 13.4 g (yield: 62.3%) of white crystals having a melting point of 92° to 93° C.

| NMR in chloroform-d₁: | |
|---|---|
| δ 1.15 ppm (t, 3H) | δ 1.46 ppm (s, 6H) |
| δ 3.00 ppm (s, 2H) | δ 3.32 ppm (s, 3H) |
| δ 4.12 ppm (q, 2H) | δ 4.76 ppm (s, 2H) |
| δ 6.5–7.5 ppm (m, 8H) | |

| Elemental Analysis: | | | |
|---|---|---|---|
| | C | H | N |
| Found (%): | 61.11 | 6.15 | 6.49 |
| Calcd. for $C_{22}H_{26}N_2O_5S$: (molecular wt. 430.53) | 61.38 | 6.09 | 6.51 |

Thus, the product was confirmed to have the following formula:

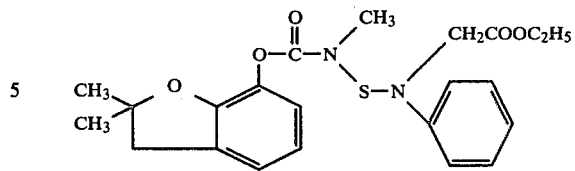

EXAMPLES 14 TO 32

The compounds shown in Table 3 below were prepared in the same manner as in Example 12 or 13. The physical properties and NMR data (in chloroform-d₁) of these compounds are also shown in Table 3.

TABLE 3

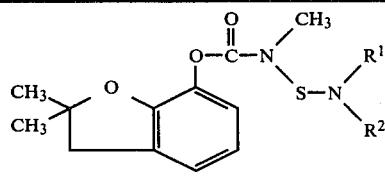

| Example No. | Amine | R¹ | R² | H-MNR [δ Value (ppm) in CDCl₃] | Elemental Analysis Empirical Formula Found Value (Calculated Value) | | |
|---|---|---|---|---|---|---|---|
| | | | | | C (%) | H (%) | N (%) |
| 14 | HN(CH₂COOC₂H₅)(CH₃) | —CH₂COOC₂H₅ | —CH₃ | δ1.24 (t, 3H), δ1.47 (s, 6H), δ3.02 (s, 2H), δ3.17 (s, 3H), δ3.48 (s, 3H), δ4.10 (s, 2H), δ4.17 (q, 2H), δ6.6–7.2 (m, 3H) | $C_{17}H_{24}N_2O_5S$ 55.61 (55.43) | 6.45 (6.56) | 7.83 (7.61) |
| 15 | HN(CH₂COOC₂H₅)(CH(CH₃)₂) | —CH₂COOC₂H₅ | —CH(CH₃)₂ | δ1.16 (d, 6H), δ1.18 (t, 3H), δ1.43 (s, 6H), δ2.94 (s, 2H), δ3.29 (s, 3H), δ3.1–3.7 (m, 1H), δ4.00 (q, 2H), δ4.02 (s, 2H), δ6.5–7.0 (m, 3H) | $C_{19}H_{28}N_2O_5S$ 57.34 (57.56) | 7.15 (7.12) | 7.17 (7.07) |
| 16 | HN(CH₂COOC₂H₅)(sec-C₄H₉) | —CH₂COOC₂H₅ | —sec-C₄H₉ | δ0.8–1.8 (m, 8H), δ1.22 (t, 3H), δ1.45 (s, 6H), δ2.97 (s, 2H), δ2.9–3.3 (m, 1H), δ3.30 (s, 3H), δ4.03 (s, 2H), δ4.08 (q, 2H), δ6.7–7.1 (m, 3H) | $C_{20}H_{30}N_2O_5S$ 58.55 (58.52) | 7.25 (7.37) | 6.91 (6.83) |
| 17 | HN(CH₂COOC₂H₅)(n-C₈H₁₇) | —CH₂COOC₂H₅ | —n-C₈H₁₇ | δ0.7–1.8 (m, 18H), δ1.45 (s, 6H), δ2.97 (s, 2H), δ3.1–3.5 (m, 2H), δ3.36 (s, 3H), δ4.01 (s, 2H), δ4.07 (q, 2H), δ6.6–7.2 (m, 3H) | $C_{24}H_{38}N_2O_5S$ 61.53 (61.78) | 8.11 (8.21) | 6.24 (6.00) |
| 18 | HN(CH₂COOC₂H₅)(cyclohexyl) | —CH₂COOC₂H₅ | cyclohexyl | δ0.7–2.4 (m, 14H), δ1.43 (s, 6H), δ2.93 (s, 2H), δ3.32 (s, 3H), δ4.06 (q, 2H), δ4.08 (s, 2H), δ6.6–7.2 (m, 3H) | $C_{22}H_{32}N_2O_5S$ 60.95 (60.53) | 7.42 (7.39) | 6.51 (6.42) |

TABLE 3-continued

[Structure: 2,2-dimethyl-2,3-dihydrobenzofuran-7-yl O-C(=O)-N(CH₃)-S-N(R¹)(R²)]

| Example No. | Amine | R¹ | R² | H-NMR [δ Value (ppm) in CDCl₃] | Elemental Analysis Empirical Formula Found Value (Calculated Value) C (%) | H (%) | N (%) |
|---|---|---|---|---|---|---|---|
| 19 | HN(CH₂COOC₂H₅)(CH₂-C₆H₅) | —CH₂COOC₂H₅ | —CH₂—C₆H₅ | δ1.22 (t, 3H), δ1.40 (s, 6H), δ2.97 (s, 2H), δ3.24 (s, 3H), δ3.82 (s, 2H), δ4.11 (q, 2H), δ4.15 (s, 2H), δ6.5–7.6 (m, 8H) | C₂₃H₂₈N₂O₅S 62.04 (62.15) | 6.39 (6.35) | 6.63 (6.30) |
| 20 | HN(CH₂COOC₂H₅)(CH₂-C₆H₄-Cl) | —CH₂COOC₂H₅ | —CH₂—C₆H₄—Cl | δ1.25 (t, 3H), δ1.42 (s, 6H), δ3.04 (s, 2H), δ3.42 (s, 3H), δ3.92 (s, 2H), δ4.21 (q, 2H), δ4.23 (s, 2H), δ6.7–7.2 (m, 3H), δ7.2–7.5 (m, 4H) | C₂₃H₂₇N₂O₅ClS 58.01 (57.67) | 5.54 (5.68) | 5.69 (5.85) |
| 21 | HN(CH₂COOC₂H₅)(m-tolyl) | —CH₂COOC₂H₅ | m-CH₃—C₆H₄— | δ1.17 (t, 3H), δ1.48 (s, 6H), δ2.35 (s, 3H), δ3.05 (s, 2H), δ3.40 (s, 3H), δ4.18 (q, 2H), δ4.80 (s, 2H), δ6.7–7.5 (m, 7H) | C₂₃H₂₈N₂O₅S 61.84 (62.15) | 6.42 (6.35) | 6.19 (6.30) |
| 22 | HN(CH₂COOC₂H₅)(p-MeO-C₆H₄) | —CH₂COOC₂H₅ | p-CH₃O—C₆H₄— | δ1.15 (t, 3H), δ1.48 (s, 6H), δ3.02 (s, 2H), δ3.31 (s, 3H), δ3.76 (s, 3H), δ4.17 (q, 2H), δ3.70 (s, 2H), δ6.7–7.4 (m, 7H) | C₂₃H₂₈N₂O₆S 60.31 (59.99) | 6.22 (6.13) | 6.11 (6.08) |
| 23 | HN(CH₂CH₂COOC₂H₅)(CH(CH₃)₂) | —CH₂CH₂COOC₂H₅ | —CH(CH₃)₂ | δ1.21 (t, 3H), δ1.23 (d, 6H), δ1.47 (s, 6H), δ2.78 (t, 2H), δ3.04 (s, 2H), δ3.40 (s, 3H), δ3.2–3.8 (m, 3H), δ4.12 (q, 2H), δ6.6–7.2 (m, 3H) | C₂₀H₃₀N₂O₅S 58.43 (58.52) | 7.29 (7.37) | 6.65 (6.83) |
| 24 | HN(CH₂CH₂COOCH₃)(CH(CH₃)₂) | —CH₂CH₂COOCH₃ | —CH(CH₃)₂ | δ1.18 (d, 6H), δ1.43 (s, 6H), δ2.68 (t, 2H), δ2.99 (s, 2H), δ3.0–3.5 (m, 3H), δ3.31 (s, 3H), δ3.51 (s, 3H), δ6.5–7.1 (m, 3H) | C₁₉H₂₈N₂O₅S 58.01 (57.56) | 7.32 (7.12) | 7.11 (7.07) |
| 25 | HN(CH₂CH₂COOC₄H₉)(CH(CH₃)₂) | —CH₂CH₂COOC₄H₉ | —CH(CH₃)₂ | δ0.6–1.8 (m, 7H), δ1.17 (d, 6H), δ1.42 (s, 6H), δ2.65 (t, 2H), δ2.94 (s, 2H), δ3.31 (s, 3H), δ3.0–3.6 (m, 3H), δ3.7–4.1 (m, 2H), δ6.5–7.0 (m, 3H) | C₂₂H₃₄N₂O₅S 60.48 (60.25) | 7.69 (7.82) | 6.13 (6.39) |

TABLE 3-continued

Structure:
2,2-dimethyl-2,3-dihydrobenzofuran-7-yl O-C(=O)-N(CH₃)-S-N(R¹)(R²)

| Example No. | Amine | R¹ | R² | H-NMR [δ Value (ppm) in CDCl₃] | Elemental Analysis Empirical Formula Found Value (Calculated Value) C (%) | H (%) | N (%) |
|---|---|---|---|---|---|---|---|
| 26 | HN(CH₂CH₂COO-CH(CH₃)₂)(CH(CH₃)₂) (isopropyl ester branch) | —CH₂CH₂COO—CH(CH₃)₂ | —CH(CH₃)₂ | δ0.6–1.8 (m, 15H), δ1.16 (d, 6H), δ1.42 (s, 6H), δ2.68 (t, 2H), δ2.98 (s, 2H), δ3.0–3.6 (m, 3H), δ3.33 (s, 3H), δ3.6–4.1 (m, 2H), δ6.5–7.0 (m, 3H) | $C_{26}H_{42}N_2O_5S$ 63.45 (63.13) | 8.62 (8.56) | 5.49 (5.66) |
| 27 | HN(CH₂CH₂COOC₂H₅)(n-C₄H₉) | —CH₂CH₂COOC₂H₅ | —n-C₄H₉ | δ0.7–1.8 (m, 10H), δ1.41 (s, 6H), δ2.4–2.8 (m, 2H), δ2.95 (s, 2H), δ3.33 (s, 3H), δ3.1–3.4 (m, 4H), δ3.97 (q, 2H), δ6.6–7.2 (m, 3H) | $C_{21}H_{32}N_2O_5S$ 59.01 (59.42) | 7.38 (7.60) | 6.79 (6.60) |
| 28 | HN(CH₂CH₂COOCH₃)(n-C₄H₉) | —CH₂CH₂COOCH₃ | —n-C₄H₉ | δ0.6–2.0 (m, 7H), δ1.45 (s, 6H), δ2.66 (t, 2H), δ2.97 (s, 2H), δ2.9–3.7 (m, 4H), δ3.35 (s, 3H), δ3.54 (s, 3H), δ6.5–7.0 (m, 3H) | $C_{20}H_{30}N_2O_5S$ 58.79 (58.52) | 7.14 (7.37) | 6.66 (6.83) |
| 29 | HN(CH₂CH₂COOC₂H₅)(sec-C₄H₉) | —CH₂CH₂COOC₂H₅ | —sec-C₄H₉ | δ0.6–1.8 (m, 11H), δ1.42 (s, 6H), δ2.66 (t, 2H), δ2.96 (s, 2H), δ3.0–3.7 (m, 3H), δ3.31 (s, 3H), δ3.95 (q, 2H), δ6.6–7.0 (m, 3H) | $C_{21}H_{32}N_2O_5S$ 59.62 (59.42) | 7.71 (7.60) | 6.53 (6.60) |
| 30 | HN(CH₂CH₂COOC₂H₅)(iso-C₄H₉) | —CH₂CH₂COOC₂H₅ | —iso-C₄H₉ | δ0.84 (d, 6H), δ1.18 (t, 3H), δ1.42 (s, 6H), δ1.6–2.2 (m, 1H), δ2.70 (t, 2H), δ2.97 (s, 2H), δ3.1–3.6 (m, 4H), δ3.37 (s, 3H), δ4.04 (q, 2H), δ6.5–7.1 (m, 3H) | $C_{21}H_{32}N_2O_5S$ 59.71 (59.42) | 7.54 (7.60) | 6.63 (6.60) |
| 31 | HN(CH₂CH₂COOC₂H₅)(n-C₆H₁₃) | —CH₂CH₂COOC₂H₅ | —n-C₆H₁₃ | δ0.7–2.0 (m, 14H), δ1.46 (s, 6H), δ2.63 (t, 2H), δ2.98 (s, 2H), δ2.9–3.6 (m, 4H), δ3.35 (s, 3H), δ3.97 (q, 2H), δ6.5–7.0 (m, 3H) | $C_{23}H_{36}N_2O_5S$ 60.85 (61.04) | 8.11 (8.02) | 6.32 (6.19) |

TABLE 3-continued

[Structure: 2,3-dihydro-2,2-dimethylbenzofuran-7-yl carbamate with sulfenyl amine group]

| Example No. | Amine | R¹ | R² | H-MNR [δ Value (ppm) in CDCl₃] | Elemental Analysis Empirical Formula Found Value (Calculated Value) C (%) | H (%) | N (%) |
|---|---|---|---|---|---|---|---|
| 32 | HN(CH₂CH₂COOC₂H₅)(C₆H₁₁) | —CH₂CH₂COOC₂H₅ | —C₆H₁₁ | δ0.9–2.0 (m, 10H), δ1.17 (t, 3H), δ1.43 (s, 6H), δ2.64 (t, 2H), δ2.94 (s, 2H), δ3.0–3.6 (m, 3H), δ2.97 (s, 3H), δ3.95 (q, 2H), δ6.5–7.1 (m, 3H) | $C_{23}H_{34}N_2O_5S$ 61.59 (61.31) | 7.49 (7.61) | 6.09 (6.22) |

EXAMPLE 33

Preparation of
2,3-dihydro-2,2-dimethylbenzofuran-7-yl
N-(N-butyl-N-cyanomethylaminosulfenyl)-N-methyl-carbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at −10° to −5° C. The mixture was stirred at 0° C. for one hour and further at room temperature for 2 hours. After cooling to −10° to −5° C., 5.6 g (0.05 mole) of N-butylaminoacetonitrile was added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product, which was almost entirely composed of the desired product although containing small amounts of impurities. Yield: 13.0 g (71.4%).

For the identification of the product, a portion thereof was purified by silica gel column chromatography, using benzene/ethyl acetate (5:1) as the solvent, whereby an oily product was obtained.

| NMR in chloroform-d₁: | |
|---|---|
| δ 0.7–2.0 ppm (m, 7H) | δ 1.42 ppm (s, 6H) |
| δ 2.92 ppm (s, 2H) | δ 2.9–3.5 ppm (m, 2H) |
| δ 3.33 ppm (s, 3H) | δ 4.01 ppm (s, 2H) |
| δ 6.5–7.1 ppm (m, 3H) | |

| Elemental Analysis: | C | H | N |
|---|---|---|---|
| Found (%): | 59.19 | 7.02 | 11.69 |
| Calcd. for $C_{18}H_{25}N_3O_3S$: (molecular wt. 363.488) | 59.48 | 6.93 | 11.56 |

Thus, the product was confirmed to have the following formula:

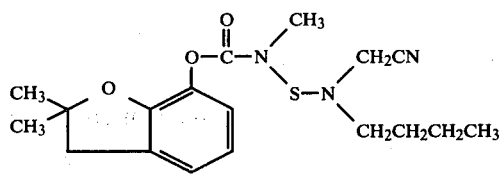

EXAMPLES 34 TO 42

The compounds shown in Table 4 below were prepared in the same manner as in Example 33. The physical properties and NMR data (in chloroform-d₁) of these compounds are also shown in Table 4.

TABLE 4

[Structure: 2,2-dimethyl-2,3-dihydrobenzofuran-7-yl N-methyl-N-(N',N'-disubstituted aminothio)carbamate with R¹ and R² on the amine nitrogen]

| Example No. | Amine | R¹ | R² | H-NMR [δ Value (ppm) in CDCl₃] | Elemental Analysis Empirical Formula Found Value (Calculated Value) C (%) H (%) N (%) |
|---|---|---|---|---|---|
| 34 | HN(CH₂CN)(CH(CH₃)₂) | —CH₂CN | —CH(CH₃)₂ | δ1.28 (d, 6H), δ1.42 (s, 6H), δ3.00 (s, 2H), δ3.43 (s, 3H), δ4.34 (s, 2H), δ3.3–4.1 (m, 1H), δ6.5–7.2 (m, 3H) | $C_{17}H_{23}N_3O_3S$ 58.23  6.59  12.21 (58.44) (6.64) (12.03) |
| 35 | HN(CH₂CN)(C₆H₅) | —CH₂CN | —C₆H₅ | δ1.44 (s, 6H), δ2.98 (s, 2H), δ3.41 (s, 3H), δ4.76 (s, 2H), δ6.5–7.7 (m, 8H) | $C_{20}H_{21}N_3O_3S$ 62.11  5.48  11.02 (62.65) (5.52) (10.96) |
| 36 | HN(CH₂CN)(p-CH₃-C₆H₄) | —CH₂CN | —C₆H₄-CH₃ | δ1.47 (s, 6H), δ2.33 (s, 3H), δ3.00 (s, 2H), δ3.39 (s, 3H), δ4.80 (s, 2H), δ6.5–7.5 (m, 7H) | $C_{21}H_{23}N_3O_3S$ 63.51  5.79  10.31 (63.46) (5.83) (10.58) |
| 37 | HN(CH₂CH₂CN)(CH₃) | —CH₂CH₂CN | —CH₃ | δ1.46 (s, 6H), δ2.5–2.9 (m, 2H), δ3.00 (s, 2H), δ3.17 (s, 3H), δ3.0–3.5 (m, 2H), δ3.46 (s, 3H), δ6.5–7.1 (m, 3H) | $C_{16}H_{21}N_3O_3S$ 57.59  6.17  12.74 (57.30) (6.31) (12.53) |
| 38 | HN(CH₂CH₂CN)(CH(CH₃)₂) | —CH₂CH₂CN | —CH(CH₃)₂ | δ1.21 (d, 6H), δ1.43 (s, 6H), δ2.72 (t, 2H), δ3.00 (s, 2H), δ3.0–3.8 (m, 3H), δ3.32 (s, 3H), δ6.6–7.2 (m, 3H) | $C_{18}H_{25}N_3O_3S$ 59.32  6.87  11.64 (59.49) (6.93) (11.56) |
| 39 | HN(CH₂CH₂CN)(n-C₄H₉) | —CH₂CH₂CN | —n-C₄H₉ | δ0.7–2.0 (m, 7H), δ1.44 (s, 6H), δ2.5–2.9 (m, 2H), δ2.98 (s, 2H), δ2.9–3.5 (m, 4H), δ3.37 (s, 3H), δ6.5–7.0 (m, 3H) | $C_{19}H_{27}N_3O_3S$ 60.64  7.41  11.25 (60.46) (7.21) (11.13) |
| 40 | HN(CH₂CH₂CN)(iso-C₄H₉) | —CH₂CH₂CN | —iso-C₄H₉ | δ0.90 (d, 6H), δ1.43 (s, 6H), δ1.7–2.2 (m, 1H), δ2.69 (t, 2H), δ2.96 (s, 2H), δ3.0–3.5 (m, 4H), δ3.33 (s, 3H), δ6.5–7.0 (m, 3H) | $C_{19}H_{27}N_3O_3S$ 60.25  7.39  11.01 (60.46) (7.21) (11.13) |
| 41 | HN(CH₂CH₂CN)(n-C₈H₁₇) | —CH₂CH₂CN | —n-C₈H₁₇ | δ0.7–2.0 (m, 15H), δ1.47 (s, 6H), δ2.6–2.9 (m, 2H), δ3.01 (s, 2H), δ3.0–3.5 (m, 4H), δ3.40 (s, 3H), δ6.5–7.0 (m, 3H) | $C_{23}H_{35}N_3O_3S$ 63.59  8.31  9.54 (63.72) (8.14) (9.69) |

TABLE 4-continued

| | | | | H-NMR [δ Value (ppm) in CDCl₃] | Elemental Analysis Empirical Formual Found Value (Calculated Value) | | |
|---|---|---|---|---|---|---|---|
| Example No. | Amine | R¹ | R² | | C (%) | H (%) | N (%) |
| 42 | HN(CH₂CH₂CN)(C₆H₁₁) | —CH₂CH₂CN | C₆H₅ | δ0.7-2.0 (m, 10H), δ1.46 (s, 6H), δ2.5-2.9 (m, 2H), δ2.98 (s, 2H), δ3.0-3.5 (m, 2H), δ3.32 (s, 3H), δ3.9-4.3 (m, 1H), δ6.5-7.1 (m, 3H) | C₂₁H₂₉N₃O₃S 62.33 (62.51) | 7.42 (7.25) | 10.85 (10.42) |

EXAMPLE 43

Preparation of 2,3-dihydro-2,2-dimethylbenzofuran-7-yl N-(N-propionyl-N-ethoxycarbonylmethylaminosulfenyl)-N-methyl-carbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at −10° to 31 5° C. The mixture was stirred at 0° C. for one hour and further at room temperature for 2 hours. After cooling to −10° to −5° C., a solution of 8 g (0.05 mole) of N-propionylglycine ethyl ester in 10 ml of methylene chloride was added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product, which was almost entirely composed of the desired product although containing small amounts of the starting materials and impurities. Yield: 14.3 g (69.8%).

For the identification of the product, a portion thereof was purified by silica gel column chromatography, using benzene/ethyl acetate (9:1) as the solvent, whereby crystals having a melting point of 108° to 109° C. were obtained.

| NMR in chloroform-d₁: | |
|---|---|
| δ 1.14 ppm (t, 3H) | δ 1.23 ppm (t, 3H) |
| δ 1.49 ppm (s, 6H) | δ 2.7-3.3 ppm (m, 2H) |
| δ 3.02 ppm (s, 2H) | δ 3.48 ppm (s, 3H) |
| δ 4.15 ppm (q, 2H) | δ 4.50 ppm (s, 2H) |
| δ 6.6-7.1 ppm (m, 3H) | |

| Elemental Analysis: | C | H | N |
|---|---|---|---|
| Found (%): | 55.35 | 6.41 | 6.77 |
| Calcd. for C₁₉H₂₆N₂O₆S: (molecular wt. 410.499) | 55.59 | 6.38 | 6.82 |

Thus, the product was confirmed to have the following formula:

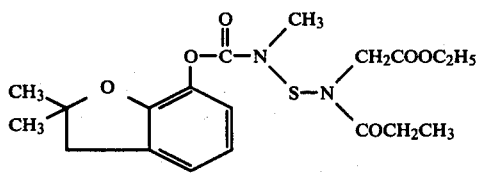

EXAMPLE 44

Preparation of 2,3-dihydro-2,2-dimethylbenzofuran-7-yl N-(N-ethoxycarbonyl-N-ethoxycarbonylmethylaminosulfenyl)-N-methyl-carbamate A 11 g quantity (0.05 mole) of 2,3-dihydro-2,2-dimethylbenzofuran-7-yl N-methyl-carbamate was dissolved in 70 ml of methylene chloride, 5.2 g (0.05 mole) of sulfur dichloride was added to the solution with cooling, and 5 g (0.05 mole) of triethylamine was further added dropwise to the solution at −10° to −5° C. The mixture was stirred at 0° C. for one hour and further at room temperature for 2 hours. After cooling to −10° to −5° C., 8.8 g (0.05 mole) of N-ethoxycarbonylglycine ethyl ester was added dropwise to the mixture, and 5 g (0.05 mole) of triethylamine was further added dropwise to the mixture. The resulting mixture was stirred at 0° C. for 2 hours and thereafter allowed to stand overnight at room temperature. With addition of 100 ml of methylene chloride, the reaction mixture was washed with 100 ml of water three times. The methylene chloride layer was dried and then concentrated in a vacuum to give an oily product, which was almost entirely composed of the desired product although containing small amounts of the starting materials and impurities. Yield: 18.2 g (84.7%).

For the identification of the product, a portion thereof was purified by silica gel column chromatography, using benzene/ethyl acetate (4:1) as the solvent, whereby an oily product was obtained.

| NMR in chloroform-d₁: | |
|---|---|
| δ 1.17 ppm (t, 6H) | δ 1.44 ppm (s, 6H) |

|  | -continued |
|---|---|
| δ 2.94 ppm (s, 2H) | δ 3.41 ppm (s, 3H) |
| δ 4.05 ppm (q, 2H) | δ 4.15 ppm (q, 2H) |
| δ 4.41 ppm (s, 2H) | δ 6.5–7.0 ppm (m, 3H) |

| Elemental Analysis: | C | H | N |
|---|---|---|---|
| Found (%): | 53.82 | 6.19 | 6.44 |
| Calcd. for $C_{19}H_{26}N_2O_7S$: (molecular wt. 426.499) | 53.51 | 6.14 | 6.57 |

Thus, the product was confirmed to have the following formula:

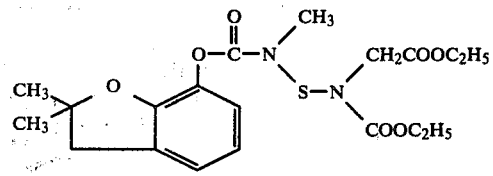

EXAMPLE 45 TO 52

The compounds shown in Table 5 below were prepared in the same manner as in Example 43 or 44. The physical properties and NMR data (in chloroform-$d_1$) of these compounds are also shown in Table 5.

TABLE 5

| Example No. | Amine | $R^1$ | $R^2$ | H-NMR [δ Value (ppm) in CDCl$_3$] | Elemental Analysis Empirical Formula Found Value (Calculated Value) C (%)   H (%)   N (%) |
|---|---|---|---|---|---|
| 45 | HN(CH$_2$COOC$_2$H$_5$)(COCH$_2$Cl) | —CH$_2$COOC$_2$H$_5$ | —COCH$_2$Cl | δ1.21 (t, 3H), δ1.46 (s, 6H), δ2.98 (s, 2H), δ3.40 (s, 3H), δ4.05 (q, 2H), δ4.36 (s, 2H), δ4.67 (s, 2H), δ6.5–7.0 (m, 3H) | $C_{18}H_{23}N_2O_6ClS$<br>49.98   5.17   6.43<br>(50.17) (5.38) (6.50) |
| 46 | HN(CH$_2$COOC$_2$H$_5$)(CO-C$_6$H$_5$) | —CH$_2$COOC$_2$H$_5$ | —CO-C$_6$H$_5$ | δ1.18 (t, 3H), δ1.41 (s, 6H), δ2.87 (s, 3H), δ2.91 (s, 2H), δ4.06 (q, 2H), δ4.60 (s, 2H), δ6.5–7.0 (m, 3H), δ7.1–7.7 (m, 5H) | $C_{23}H_{26}N_2O_6S$<br>60.54   5.61   6.02<br>(60.25) (5.72) (6.11) |
| 47 | HN(CH$_2$COOC$_2$H$_5$)(CO-C$_6$H$_4$-Cl) | —CH$_2$COOC$_2$H$_5$ | —CO-C$_6$H$_4$-Cl | δ1.21 (t, 3H), δ1.46 (s, 6H), δ2.93 (s, 3H), δ2.95 (s, 2H), δ4.07 (q, 2H), δ4.56 (s, 2H), δ6.5–7.0 (m, 3H), δ7.1–7.6 (m, 4H) | $C_{23}H_{25}N_2O_6ClS$<br>56.53   5.37   5.49<br>(56.04) (5.11) (5.68) |
| 48 | HN(CH$_2$COOC$_2$H$_5$)(SO$_2$-C$_6$H$_4$-CH$_3$) | —CH$_2$COOC$_2$H$_5$ | —SO$_2$-C$_6$H$_4$-CH$_3$ | δ1.18 (t, 3H), δ1.46 (s, 6H), δ2.37 (s, 3H), δ2.96 (s, 2H), δ3.48 (s, 3H), δ4.02 (q, 2H), δ4.58 (s, 2H), δ6.5–7.9 (m, 7H) | $C_{23}H_{28}N_2O_7S_2$<br>54.04   5.57   5.24<br>(54.31) (5.55) (5.51) |
| 49 | HN(CH$_2$COOC$_2$H$_5$)(COOCH$_3$) | —CH$_2$COOC$_2$H$_5$ | —COOCH$_3$ | δ1.19 (t, 3H), δ1.46 (s, 6H), δ2.97 (s, 2H), δ3.43 (s, 3H), δ3.74 (s, 3H), δ4.07 (q, 2H), δ4.42 (s, 2H), δ6.5–7.1 (m, 3H) | $C_{18}H_{24}N_2O_7S$<br>52.15   5.64   6.66<br>(52.42) (5.87) (6.79) |

TABLE 5-continued

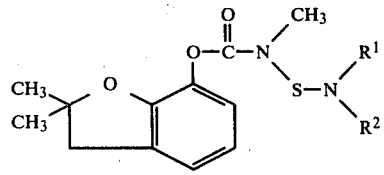

| Example No. | Amine | R$^1$ | R$^2$ | H-NMR [δ Value (ppm) in CDCl$_3$] | Elemental Analysis Empirical Formula Found Value (Calculated Value) | | |
|---|---|---|---|---|---|---|---|
| | | | | | C (%) | H (%) | N (%) |
| 50 | HN(CH$_2$COOC$_2$H$_5$)(COO-Ph) | —CH$_2$COOC$_2$H$_5$ | —COO-Ph | δ1.19 (t, 3H), δ1.44 (s, 6H), δ2.95 (s, 2H), δ3.50 (s, 3H), δ4.05 (q, 2H), δ4.52 (s, 2H), δ6.5–7.4 (m, 8H) | C$_{23}$H$_{26}$N$_2$O$_7$S 57.97 (58.22) | 5.61 (5.52) | 5.78 (5.90) |
| 51 | HN(CH$_2$CH$_2$CN)(COOC$_2$H$_5$) | —CH$_2$CH$_2$CN | —COOC$_2$H$_5$ | δ1.30 (t, 3H), δ1.46 (s, 6H), δ2.63 (t, 2H), δ2.97 (s, 2H), δ3.40 (s, 3H), δ3.95 (t, 2H), δ4.16 (q, 2H), δ6.5–7.0 (m, 3H) | C$_{18}$H$_{23}$N$_3$O$_5$S 55.16 (54.95) | 5.93 (5.89) | 10.31 (10.68) |
| 52 | HN(CH$_2$CH$_2$COOC$_2$H$_5$)(COOC$_2$H$_5$) | —CH$_2$CH$_2$COOC$_2$H$_5$ | —COOC$_2$H$_5$ | δ1.17 (t, 3H), δ1.32 (t, 3H), δ1.46 (s, 6H), δ2.57 (t, 2H), δ2.98 (s, 2H), δ3.40 (s, 3H), δ3.7–4.4 (m, 6H), δ6.5–7.0 (m, 3H) | C$_{20}$H$_{28}$N$_2$O$_7$S 54.33 (54.54) | 6.29 (6.41) | 6.51 (6.36) |

Preparation Examples of this invention are given below. These prescriptions are applicable to all the compounds of this invention; a suitable prescription is usable for a particular application. The prescriptions are shown only for illustrative purposes, and the proportions of the active component, organic solvent, surfactant and carrier are variable as desired. In some cases, the kinds of organic solvent, surfactant, carrier, etc., can also be changed. The percentages are all by weight.

PREPARATION EXAMPLE 1

| 60% Emulsion: | |
|---|---|
| Compound of Example 25 | 60.0% |
| Polyoxyethylene nonylphenyl ether | 10.0 |
| Xylene | 30.0 |

PREPARATION EXAMPLE 2

| 50% Emulsion: | |
|---|---|
| Compound of Example 12 | 50.0% |
| Polyoxyethylene sorbitan monooleate | 6.5 |
| Sorbitan monooleate | 3.5 |
| Xylene | 30.0 |
| Cyclohexanone | 10.0 |

PREPARATION EXAMPLE 3

| 20% Emulsion: | |
|---|---|
| Compound of Example 22 | 20.0% |
| Polyoxyethylene alkyl ether | 5.0 |
| Xylene | 45.0 |
| Petroleum ether | 30.0 |

In each of Preparation Examples 1 to 3, the ingredients were uniformly mixed and dissolved to obtain the desired emulsion.

PREPARATION EXAMPLE 4

| 90% Wettable powder: | |
|---|---|
| Compound of Example 1 | 90.0% |
| Sodium lignin sulfonate | 3.0 |
| Clay | 7.0 |

PREPARATION EXAMPLE 5

| 50% Wettable powder: | |
|---|---|
| Compound of Example 21 | 50.0% |
| Alkyl sulfate | 30.0 |
| Condensate of naphthalenesulfonic acid and formaldehyde | 10.0 |
| Alkyl phosphate | 5.5 |
| Kaolin | 3.5 |
| Talc | 1.0 |

PREPARATION EXAMPLE 6

30% Wettable powder

-continued

| Compound of Example 30 | 30.0% |
|---|---|
| Alkylbenzenesulfonate | 3.0 |
| Sodium lignin sulfonate | 2.0 |
| White carbon | 15.0 |
| Clay | 50.0 |

In each of Preparation Examples 4 to 6, the ingredients were uniformly mixed with stirring using a Shinagawa-type mixer. The mixture was then finely pulverized using a sample mill or ball mill to obtain the desired wettable powder.

PREPARATION EXAMPLE 7

| 5% Dust: | |
|---|---|
| Compound of Example 46 | 5.0% |
| Diatomaceous earth | 10.0 |
| Talc | 85.0 |

PREPARATION EXAMPLE 8

| 2% Dust: | |
|---|---|
| Wettable powder of Preparation Example 5 | 4.0% |
| Clay | 95.8 |
| Isopropyl phosphate | 0.2 |

PREPARATION EXAMPLE 9

| 0.5% Dust: | |
|---|---|
| Wettable powder of Preparation Example 6 | 1.7% |
| Clay | 100.3 |

In each of Preparation Examples 7 to 9, the ingredients were uniformly mixed with stirring using a Shinagawa-type mixer to obtain the desired dust.

PREPARATION EXAMPLE 10

| 20% Granule: | |
|---|---|
| Wettable powder of Preparation Example 5 | 40.0% |
| Dolomite | 60.0% |

These ingredients were uniformly mixed, a 2% aqueous solution of carboxymethyl cellulose was added to the mixture in an amount of 15 parts by weight per 100 parts by weight of the mixture, and the resulting mixture was thoroughly kneaded. The mixture was then granulated using a granulator and finely cleaved, followed by allowing it to dry. Thus, the desired granule was obtained.

PREPARATION EXAMPLE 11

| 10% Granule: | |
|---|---|
| Compound of Example 40 | 10.0% |
| Sodium dodecylbenzenesulfonate | 0.5 |
| Sodium lignin sulfonate | 2 |
| Diatomaceous earth | 27.5 |
| Bentonite | 60.0 |

These ingredients were uniformly mixed, and water was added to the mixture. The resulting mixture was thoroughly kneaded, and then granulated using a granulator. The thus-granulated product was finely cleaved and dried to obtain the desired granule.

PREPARATION EXAMPLE 12

| 3% Granule: | |
|---|---|
| Compound of Example 8 | 3.0% |
| Polyvinyl alcohol | 3.0 |
| Clay | 94.0 |

The same procedure as in Preparation Example 11 was repeated to obtain the desired granule.

Test Examples are given below.

TEST EXAMPLE 1

Ten third-instar larvae of tobacco cutworm (*Spodoptera litura*) were placed on a cabbage (one-month-old seedling) planted in a pot, and a 50% emulsion of the compound to be tested was diluted to a specified concentration and applied to the leaves of the plant to fully wet them. The test compound of each specified concentration was tested on two pots. Three days later, the larvae were checked for mortality, with the result listed in Table 6, which also shows the results achieved for control groups and untreated groups for comparison.

TABLE 6

| Test Compound (Example No.) | Mortality (%) Concentration of Active Ingredient (ppm) | | |
|---|---|---|---|
| | 2,000 | 1,000 | 500 |
| 1 | 100 | 80 | 65 |
| 2 | 100 | 70 | 60 |
| 3 | 100 | 80 | 65 |
| 4 | 100 | 70 | 60 |
| 5 | 100 | 80 | 65 |
| 6 | 100 | 75 | 60 |
| 7 | 100 | 75 | 60 |
| 8 | 100 | 85 | 75 |
| 9 | 100 | 90 | 80 |
| 10 | 100 | 85 | 75 |
| 11 | 100 | 80 | 70 |
| 12 | 100 | 90 | 75 |
| 13 | 100 | 90 | 75 |
| 14 | 100 | 90 | 75 |
| 15 | 100 | 90 | 75 |
| 16 | 100 | 85 | 65 |
| 17 | 100 | 80 | 60 |
| 18 | 100 | 90 | 75 |
| 19 | 100 | 85 | 65 |
| 20 | 100 | 85 | 65 |
| 21 | 100 | 90 | 75 |
| 22 | 100 | 85 | 65 |
| 23 | 100 | 85 | 70 |
| 24 | 100 | 85 | 75 |
| 25 | 100 | 90 | 75 |
| 26 | 100 | 80 | 60 |
| 27 | 100 | 90 | 75 |
| 28 | 100 | 90 | 75 |
| 29 | 100 | 80 | 60 |
| 30 | 100 | 85 | 65 |
| 31 | 100 | 80 | 60 |
| 32 | 100 | 80 | 65 |
| 33 | 100 | 90 | 75 |
| 34 | 100 | 90 | 75 |
| 35 | 100 | 80 | 65 |
| 36 | 100 | 80 | 65 |
| 37 | 100 | 85 | 70 |
| 38 | 100 | 90 | 75 |
| 39 | 100 | 90 | 75 |
| 40 | 100 | 85 | 75 |
| 41 | 100 | 80 | 65 |
| 42 | 100 | 85 | 70 |

TABLE 6-continued

| Test Compound | Mortality (%) Concentration of Active Ingredient (ppm) | | |
|---|---|---|---|
| (Example No.) | 2,000 | 1,000 | 500 |
| 43 | 100 | 85 | 70 |
| 44 | 100 | 90 | 75 |
| 45 | 100 | 90 | 75 |
| 46 | 100 | 85 | 70 |
| 47 | 100 | 80 | 65 |
| 48 | 100 | 80 | 65 |
| 49 | 100 | 90 | 75 |
| 50 | 100 | 80 | 65 |
| 51 | 100 | 85 | 70 |
| 52 | 100 | 85 | 70 |
| Control* | 100 | 80 | 60 |
| Untreated | | 0 | |

*1-Naphthyl-N—methyl-carbamate was used as the control.

TEST EXAMPLE 2

An emulsion of specified concentration was prepared from a 50% wettable powder of the compound to be tested and applied to the leaves of paddy rice (one-month-old seedlings) planted in a pot to fully wet the leaves. After the emulsion had been dried, the pot was covered with a net cage, into which 10 female adults of green rice leafhopper (*Nephotettix cincticeps*) were released. The compound of each specified concentration was tested on two pots. Three days later, the insects were checked for mortality, with the result listed in Table 7, which also shows the results achieved for control groups and untreated groups for comparison.

TABLE 7

| Test Compound | Mortality (%) Concentration of Active Ingredient (ppm) | | |
|---|---|---|---|
| (Example No.) | 800 | 400 | 200 |
| 1 | 100 | 85 | 50 |
| 2 | 100 | 85 | 45 |
| 3 | 100 | 85 | 45 |
| 4 | 100 | 70 | 40 |
| 5 | 100 | 80 | 45 |
| 6 | 95 | 75 | 55 |
| 7 | 90 | 70 | 50 |
| 8 | 95 | 85 | 60 |
| 9 | 100 | 90 | 60 |
| 10 | 100 | 90 | 60 |
| 11 | 95 | 80 | 55 |
| 12 | 100 | 90 | 65 |
| 13 | 100 | 90 | 65 |
| 14 | 100 | 90 | 65 |
| 15 | 100 | 90 | 65 |
| 16 | 100 | 80 | 60 |
| 17 | 95 | 75 | 55 |
| 18 | 100 | 90 | 65 |
| 19 | 100 | 80 | 60 |
| 20 | 100 | 80 | 60 |
| 21 | 100 | 90 | 65 |
| 22 | 100 | 80 | 60 |
| 23 | 100 | 85 | 55 |
| 24 | 100 | 90 | 60 |
| 25 | 100 | 90 | 65 |
| 26 | 100 | 75 | 55 |
| 27 | 100 | 90 | 65 |
| 28 | 100 | 90 | 65 |
| 29 | 100 | 75 | 45 |
| 30 | 100 | 80 | 60 |
| 31 | 100 | 75 | 55 |
| 32 | 100 | 75 | 55 |
| 33 | 100 | 90 | 70 |
| 34 | 100 | 90 | 65 |
| 35 | 95 | 75 | 60 |
| 36 | 95 | 75 | 60 |
| 37 | 100 | 85 | 65 |
| 38 | 100 | 90 | 70 |

TABLE 7-continued

| Test Compound | Mortality (%) Concentration of Active Ingredient (ppm) | | |
|---|---|---|---|
| (Example No.) | 800 | 400 | 200 |
| 39 | 100 | 90 | 70 |
| 40 | 100 | 85 | 70 |
| 41 | 95 | 75 | 60 |
| 42 | 100 | 85 | 65 |
| 43 | 100 | 85 | 60 |
| 44 | 100 | 90 | 70 |
| 45 | 100 | 90 | 65 |
| 46 | 100 | 85 | 65 |
| 47 | 95 | 75 | 60 |
| 48 | 95 | 75 | 60 |
| 49 | 100 | 90 | 70 |
| 50 | 95 | 75 | 60 |
| 51 | 100 | 85 | 65 |
| 52 | 100 | 85 | 65 |
| Control* | 0 | 0 | 0 |
| Untreated | | 0 | |

*2-Isopropoxyphenyl-N—methyl-carbamate was used as the control.

TEST EXAMPLE 3

Granules containing 10% of the compound to be tested were mixed, in a specified amount, with soil contaminated with larvae of southern root-knot nematode (*Meloidogyne incognita*), and tomato seedlings were immediately transplanted in the soil. One month later, the roots of the plant were checked for the formation of nodules. Two test areas, $2 \times 2$ m² each, were used for the compound as applied in each specified amount. The degree of formation of the nodules was determined according to the criteria given below, with the result shown in Table 8. For comparison, Table 8 also shows the results achieved in control areas and untreated areas.

| Degree of formation of nodules | |
|---|---|
| 0: 0%, | 1: Up to 25%, |
| 2: Up to 50%, | 3: Up to 75%, |
| 4: Up to 100% | |

TABLE 8

| Test Compound | Degree of Formation of Nodules Amount of Granules Applied (kg/10 a) | | |
|---|---|---|---|
| (Example No.) | 100 | 50 | 20 |
| 1 | 0 | 1 | 2 |
| 2 | 0 | 2 | 3 |
| 3 | 0 | 2 | 3 |
| 4 | 0 | 2 | 3 |
| 5 | 0 | 2 | 3 |
| 6 | 1 | 2 | 3 |
| 7 | 1 | 3 | 3 |
| 8 | 1 | 1 | 2 |
| 9 | 0 | 1 | 2 |
| 10 | 0 | 1 | 2 |
| 11 | 1 | 2 | 3 |
| 12 | 0 | 1 | 2 |
| 13 | 0 | 1 | 2 |
| 14 | 0 | 1 | 2 |
| 15 | 0 | 1 | 2 |
| 16 | 0 | 1 | 3 |
| 17 | 0 | 1 | 3 |
| 18 | 0 | 1 | 2 |
| 19 | 0 | 1 | 2 |
| 20 | 0 | 1 | 3 |
| 21 | 0 | 1 | 2 |
| 22 | 0 | 1 | 3 |
| 23 | 0 | 1 | 2 |
| 24 | 0 | 0 | 1 |

TABLE 8-continued

| Test Compound (Example No.) | Degree of Formation of Nodules Amount of Granules Applied (kg/10 a) | | |
|---|---|---|---|
| | 100 | 50 | 20 |
| 25 | 0 | 1 | 2 |
| 26 | 0 | 1 | 2 |
| 27 | 0 | 1 | 2 |
| 28 | 0 | 0 | 1 |
| 29 | 0 | 1 | 2 |
| 30 | 0 | 1 | 2 |
| 31 | 0 | 2 | 3 |
| 32 | 0 | 2 | 3 |
| 33 | 0 | 0 | 1 |
| 34 | 0 | 0 | 1 |
| 35 | 0 | 1 | 3 |
| 36 | 0 | 1 | 3 |
| 37 | 0 | 1 | 2 |
| 38 | 0 | 0 | 1 |
| 39 | 0 | 0 | 1 |
| 40 | 0 | 1 | 1 |
| 41 | 0 | 1 | 3 |
| 42 | 0 | 1 | 2 |
| 43 | 0 | 1 | 2 |
| 44 | 0 | 0 | 1 |
| 45 | 0 | 1 | 2 |
| 46 | 0 | 1 | 2 |
| 47 | 0 | 1 | 3 |
| 48 | 0 | 1 | 3 |
| 49 | 0 | 0 | 1 |
| 50 | 0 | 1 | 3 |
| 51 | 0 | 1 | 2 |
| 52 | 0 | 1 | 2 |
| Control* | 2 | 4 | 4 |
| Untreated | | 4 | |

*Bis(2-chloro-1-methylethyl)ether was used as the control.

TEST EXAMPLE 4

The compound to be tested was dissolved in a predetermined amount of acetone. The solution was diluted to various concentrations and locally applied to house fly (*Musca domestica*). Table 9 shows $LD_{50}$ values determined by the Probit method from the mortality 24 hours later.

TABLE 9

| Test Compound (Example No.) | $LD_{50}$ ($\mu g/g$) |
|---|---|
| 1 | 21.3 |
| 2 | 58.8 |
| 3 | 40.0 |
| 4 | 28.9 |
| 5 | 75.6 |
| 6 | 38.3 |
| 7 | 54.0 |
| 8 | 24.6 |
| 9 | 31.7 |
| 10 | 46.0 |
| 11 | 93.9 |
| 12 | 16.7 |
| 13 | 12.5 |
| 14 | 9.9 |
| 15 | 33.0 |
| 16 | 44.4 |
| 17 | 42.3 |
| 18 | 32.5 |
| 19 | 22.2 |
| 20 | 61.9 |
| 21 | 10.4 |
| 22 | 45.2 |
| 23 | 44.3 |
| 24 | 38.6 |
| 25 | 50.1 |
| 26 | 64.7 |
| 27 | 13.8 |
| 28 | 17.7 |
| 29 | 22.5 |

TABLE 9-continued

| Test Compound (Example No.) | $LD_{50}$ ($\mu g/g$) |
|---|---|
| 30 | 23.8 |
| 31 | 33.1 |
| 32 | 32.7 |
| 33 | 9.1 |
| 34 | 16.7 |
| 35 | 65.6 |
| 36 | 59.3 |
| 37 | 11.8 |
| 38 | 17.5 |
| 39 | 13.7 |
| 40 | 37.9 |
| 41 | 54.6 |
| 42 | 46.0 |
| 43 | 14.4 |
| 44 | 16.2 |
| 45 | 29.2 |
| 46 | 33.2 |
| 47 | 57.8 |
| 48 | 58.6 |
| 49 | 15.7 |
| 50 | 34.7 |
| 51 | 45.3 |
| 52 | 54.3 |
| Control* | 22.5 |

*2-Isopropoxyphenyl-N—methyl-carbamate was used as the control.

TEST EXAMPLE 5

Compounds of this invention were tested on male mice for acute toxicity by oral administration. Table 10 shows $LD_{50}$ values determined by the Litchfield-Wilcoxon method from the mortality on the seventh day.

TABLE 10

| Test Compound (Example No.) | $LD_{50}$ (mg/kg) |
|---|---|
| 1 | 58 |
| 2 | 140 |
| 3 | 145 |
| 4 | 122 |
| 5 | 90 |
| 6 | 135 |
| 7 | 75 |
| 8 | 105 |
| 9 | 158 |
| 10 | 115 |
| 11 | 93 |
| 12 | 125 |
| 13 | 115 |
| 14 | 120 |
| 15 | 110 |
| 16 | 110 |
| 17 | 69 |
| 18 | 135 |
| 19 | 108 |
| 20 | 75 |
| 21 | 105 |
| 22 | 88 |
| 23 | 113 |
| 24 | 77 |
| 25 | 123 |
| 26 | 150 |
| 27 | 105 |
| 28 | 89 |
| 29 | 120 |
| 30 | 133 |
| 31 | 135 |
| 32 | 107 |
| 33 | 103 |
| 34 | 95 |
| 35 | 95 |
| 36 | 70 |
| 37 | 65 |
| 38 | 125 |
| 39 | 110 |
| 40 | 103 |
| 41 | 105 |

TABLE 10-continued

| Test Compound (Example No.) | LD$_{50}$ (mg/kg) |
| --- | --- |
| 42 | 88 |
| 43 | 43 |
| 44 | 128 |
| 45 | 80 |
| 46 | 105 |
| 47 | 95 |
| 48 | 80 |
| 49 | 105 |
| 50 | 95 |
| 51 | 88 |
| 52 | 125 |
| Control* | 5.6 |

*2,3-Dihydro-2,2-dimethyl-7-benzofuran-7-yl-methyl-carbamate was used as the control.

We claim:

1. A carbamate derivative represented by the formula (I):

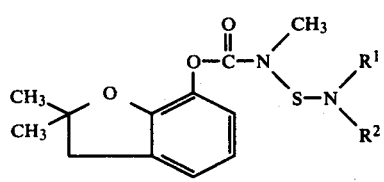

wherein $R^1$ and $R^2$, which may be the same or different, each represents (1) —X—COOR$^3$, in which X represents an alkylene group having 1 to 6 carbon atoms, and $R^3$ represents an alkyl group having 1 to 8 carbon atoms or a cycloalkyl group having 3 to 6 carbon atoms; or (2) —Y—CN, in which Y represents an alkylene group having 1 to 6 carbon atoms; and $R^2$ further represents an alkyl group having 1 to 8 carbon atoms; a cycloalkyl group having 3 to 6 carbon atoms; a benzyl group which may be substituted with a halogen atom, an alkyl group having 1 to 3 carbon atoms or an alkoxy group having 1 to 3 carbon atoms; a phenyl group which may be substituted with a halogen atom, an alkyl group having 1 to 3 carbon atoms or an alkoxy group having 1 to 3 carbon atoms; or —Z—R$^4$, in which Z represents a carbonyl group or a sulfonyl group, and $R^4$ represents an alkyl group having 1 to 6 carbon atoms which may be substituted with a halogen atom, a phenyl group which may be substituted with a halogen atom, an alkyl group having 1 to 3 carbon atoms or an alkoxy group having 1 to 3 carbon atoms, a benzyl group, an alkoxy group having 1 to 6 carbon atoms or a phenoxy group.

2. A carbamate derivative represented by the formula (I'):

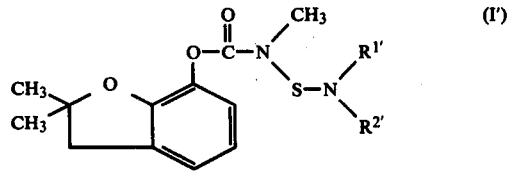

wherein $R^{1'}$ and $R^{2'}$, which may be the same or different, each represents (1) —X'—COOR$^{3'}$, in which X' represents an alkylene group having 1 or 2 carbon atoms, and $R^{3'}$ represents an alkyl group having 1 to 4 carbon atoms which may be straight chain or branched chain; or (2) —Y'—CN, in which Y' represents an alkylene group having 1 or 2 carbon atoms; and $R^{2'}$ further represents an alkyl group having 1 to 6 carbon atoms; or a cycloalkyl group having 3 to 6 carbon atoms.

3. 2,3-Dihydro-2,2-dimethylbenzofuran-7-yl N-[N,N-bis(ethoxycarbonylmethyl)aminosulfenyl]-N-methyl-carbamate, according to claim 1 or 2.

4. 2,3-Dihydro-2,2-dimethylbenzofuran-7-yl N-(N-methyl-N-ethoxycarbonylmethylaminosulfenyl)-N-methyl-carbamate, according to claim 1 or 2.

5. 2,3-Dihydro-2,2-dimethylbenzofuran-7-yl N-(N-isopropyl-N-ethoxycarbonylethylaminosulfenyl)-N-methyl-carbamate, according to claim 1 or 2.

6. 2,3-Dihydro-2,2-dimethylbenzofuran-7-yl N-(N-n-butyl-N-ethoxycarbonylethylaminosulfenyl)-N-methyl-carbamate, according to claim 1 or 2.

7. 2,3-Dihydro-2,2-dimethylbenzofuran-7-yl N-(N-cyclohexyl-N-ethoxycarbonylethylaminosulfenyl)-N-methyl-carbamate, according to claim 1 or 2.

8. 2,-Dihydro-2,2-dimethylbenzofuran-7-yl N-(N-n-butyl-N-cyanoethylaminosulfenyl)-N-methyl-carbamate, according to claim 1 or 2.

9. An insecticidal, miticidal or nematocidal composition comprising an insecticidally, miticidally or nematocidally effective amount of the carbamate derivative according to claim 1 as an active ingredient and an insecticidally, miticidally, or nematocidally acceptable material selected from the group consisting of solvents, diluting agents and carriers.

10. An insecticidal, miticidal or nematocidal composition comprising an insecticidally, miticidally or nematocidally effective amount of the carbamate derivative according to claim 2 as an active ingredient and an insecticidally, miticidally, or nematocidally acceptable material selected from the group consisting of solvents, diluting agents and carriers.

11. A method for controlling noxious insects, mites or nematodes applying thereto an insecticidally, miticidally, or nematocidally effective amount of the carbamate derivative according to claim 1.

12. A method for controlling noxious insects, mites or nematodes by applying thereto an insecticidally, miticidally, or nematocidally effective amount of the carbamate derivative according to claim 2.

* * * * *